United States Patent [19]
Li et al.

[11] Patent Number: 5,855,882
[45] Date of Patent: Jan. 5, 1999

[54] METHODS FOR INHIBITING THE CROSS-LINKING OF ADVANCED GLYCOSYLATION ENDPRODUCTS

[75] Inventors: Yong Ming Li, Fresh Meadows; Helen Vlassara; Anthony Cerami, both of Shelter Island, all of N.Y.

[73] Assignee: The Picower Institute for Medical Research, Manhasset, N.Y.

[21] Appl. No.: 485,948

[22] Filed: Jun. 7, 1995

Related U.S. Application Data

[63] Continuation of Ser. No. 418,642, Apr. 7, 1995, abandoned.
[51] Int. Cl.[6] ............................ A61K 38/47; A61K 38/16
[52] U.S. Cl. ............................................. 424/94.61; 514/9
[58] Field of Search .................. 435/206; 424/94.61; 514/2, 8, 9; 530/394, 395, 400

[56] References Cited

U.S. PATENT DOCUMENTS

| | | | |
|---|---|---|---|
| 4,908,446 | 3/1990 | Ulrich et al. | 540/553 |
| 4,983,604 | 1/1991 | Ulrich et al. | 514/238.5 |
| 5,128,360 | 7/1992 | Cerami et al. | 514/400 |

FOREIGN PATENT DOCUMENTS

| | | |
|---|---|---|
| 0474506 | 3/1992 | European Pat. Off. . |
| 0629347 | 12/1994 | European Pat. Off. . |
| WO 93/04086 | 3/1992 | WIPO . |
| WO 95/20979 | 8/1995 | WIPO . |

OTHER PUBLICATIONS

Li et al. (1995) Nature Medicine 1:1057–61.
Schmidt et al. (1995) Nature Medicine 1:1002–4.
Taylor et al. (1995) Clin. Exp. Immunol. 102:406–16.
Moshchin'ski et al. (1990) Lab Delo (USSR)(6):57–60 (Medline Abstract).
Moszczyniski et al. (1990) Pol. Arch. Med. Wewn. (Poland) 83(4–6):194–9 (Medline Abstract).
Wagnerova et al. (1988) J. Hyg. Epidemiol. Microbiol. Immunol. (Czechoslovakia) 32(3):265–72 (Medline Abstract).
Olson et al. (1985) J. Dent. Res. 64(5):826–30 (Medline Abstract).
Wagnerova et al. (1986) Czech. Med. 9(4):210–7 (Medline Abstract).
Wagner et al. (1987) Czech. Med. 10(2):70–8 (Medline Abstract).
Moszczyniski, P. (1992) Wiad. Lek. (Poland) 45(4–6):180–4 (Abstract).
Moszczyniski et al. (1991) Gig. Tr. Prof. Zabol. (USSR) 3:34–6 (Abstract).
Moszczyniski et al. (1991) Pneumonol. Alergol. Pol. (Poland) 59:17–21 (Medline Abstract).
Thompson et al. (1990 J. Lab. Clin. Med. 115:148–58 (Medline Abstract).
Knibbs et al. (1993) J. Biol. Chem. 268:14940–7.

*Primary Examiner*—Jon P. Weber
*Attorney, Agent, or Firm*—Klauber & Jackson

[57] ABSTRACT

The present invention is directed to methods for inhibiting the cross-linking of advanced glycosylation endproducts in a subject suspected of having elevated levels of AGEs by using the unexpected discovery that certain antibacterial proteins, in particular lysozyme and particular fragments thereof, bind to advanced glycosylation endproducts (AGEs) with high affinity, and that this binding activity is substantially noncompetitive with binding of bacterial carbohydrates to the antibacterial proteins. Accordingly, the invention relates to therapeutic methods for treating diseases and disorders associated with increased levels of AGEs, by using compositions having associated therewith a molecule having a hydrophilic loop domain, which domain is associated with AGE-binding activity, and compositions comprising such a domain to remove AGEs from biological material. The invention further relates to compositions for inhibiting the cross-linking of AGEs in a subject in need of such therapy.

4 Claims, 12 Drawing Sheets

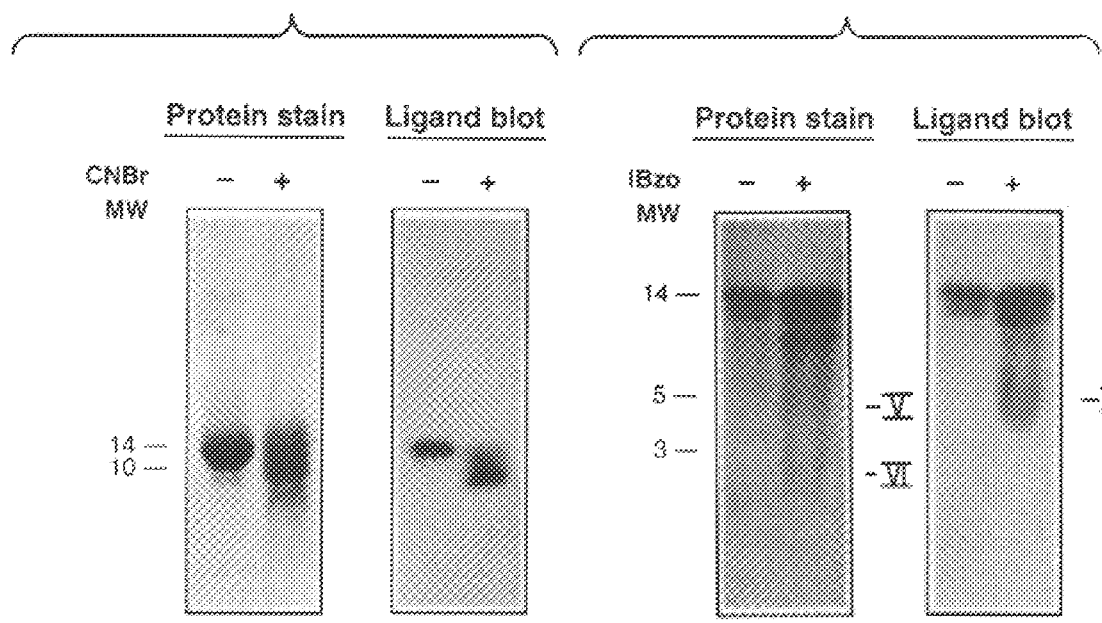

* AGE-Binding domain

FIG. 4C

```
Protein    0----------------------------------------710
 (A.A)

CNBr       0--46-------------441----493----612-622----710
 Cut
Fragments  5         40*            8.7    13         10*
 (kDa)                                     605
V8 cut     0--------240-245--------505-530↓--------710
 (kDa)        22*          26                 18*
```

\* AGE-Binding domain

```
LZ-C1   CNDGRIPGSRNLCNIPC
        62              78
LF-C1   CFQWQRNMRKVRGPPVSC
        27               46
LF-C2   CLFQSETKNLLFNDNTEC
        632              649
```

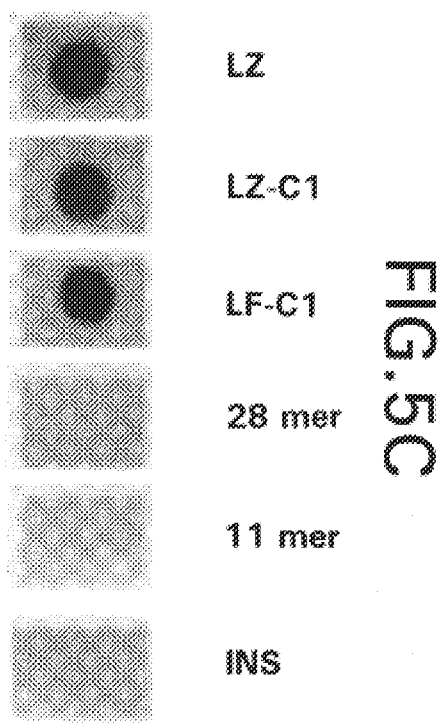

METHODS FOR INHIBITING THE CROSS-LINKING OF ADVANCED GLYCOSYLATION ENDPRODUCTS

This application is a continuation of application Ser. No. 08/418,642, filed Apr. 7, 1995, now abandoned.

TECHNICAL FIELD OF THE INVENTION

The present invention generally relates to non-enzymatic glycosylation of proteins and particularly to agents that may be interactive with glycosylated proteins and that may affect the location and activity of such proteins.

BACKGROUND OF THE INVENTION

Advanced glycosylation endproducts (AGEs) represent a heterogeneous class of reactive products which form spontaneously in vivo from the non-enzymatic reaction of glucose and proteins (Monnier et al., 1981, Science 211: 491; Bucala et al., 1992, Advanced glycosylation endproducts, Harding and Crabbe, eds., In Post-Translational Modifications of Proteins, CRC Press Inc. 2: 53–79). Glucose and other reducing sugars react non-enzymatically with the amino groups of proteins in a concentration-dependent manner. Over time, these initial Amadori adducts undergo further rearrangements, dehydrations and cross-linking with other proteins to accumulate as a family of complex structures which are referred to as Advanced Glycosylation Endproducts (AGEs). Although this chemistry has been studied by food chemists for many years, it was only in the past decade that the presence of AGEs in living tissue has been established. The excessive deposition of these products on structural proteins as a function of age and elevated glucose concentration, taken together with evidence of effective prevention of tissue pathology by an AGE inhibitor, aminoguanidine, has lent support to the hypothesis that the formation of AGEs plays a role in the long term complications of aging and diabetes.

In vivo formation of AGE-proteins proceeds slowly under normal ambient glucose concentrations, while the rate of AGE accumulation is markedly accelerated in the presence of hyperglycemia, as occurs in diabetes mellitus (Monnier and Cerami, 1983, Biochim. Biophys. Acta 760: 97–103; Monnier et al., 1984, Proc. Nati. Acad. Sci. USA 81: 583–87). Numerous studies suggest that AGEs play an important role in the structural and functional alterations which occur in senescence and long-term diabetes (Brownlee et al., 1988, N. Engl. J. Med. 318: 1315–21).

Increased levels of AGEs in tissue and serum of hyperglycemic patients have been pathogenetically linked to numerous diabetic complications, such as vascular damage and nephropathy (Vlassara et al., 1994, Lab. Invest. 70: 138). Diabetic patients also exhibit increased susceptibility to bacterial infections; however, early studies failed to demonstrate a significant adverse effect of diabetes-associated metabolic disturbances, e.g. hyperglycemia, on defense system function or bacterial growth (Moutshen et al., 1992, Diabetes and Metabolisme 18: 187). We hypothesize that elevated levels of AGE may serve as a mediator to suppress normal defense in diabetic patients.

More generally, research on the binding properties and receptors for AGE-modified proteins has not heretofore identified a particular binding domain or motif responsible for AGE recognition, contact or binding. It is appreciated that such a discovery would greatly facilitate the development of effective strategies for both diagnostic and therapeutic modalities to deal with the adverse sequelae that have observed and extensively reported. It is therefore toward such a discovery that the present invention is directed.

SUMMARY OF THE INVENTION

In accordance with the present invention, a particular binding motif for advanced glycosylation endproducts (AGEs) has been determined with respect to endogenous antibacterial proteins, that is believed to represent more comprehensively, a focal point for the molecular control of AGE binding activity. As such, the present invention contemplates the development of agents, compositions containing them, and a variety of uses that capitalize on this binding activity.

More particularly, the conserved binding motif comprises a common 17–18 amino acid cysteine-bounded hydrophilic peptide loop domain, initially discovered and identified in the antibacterial proteins lysozyme and lactoferrin. These cysteine loop domains have been prepared synthetically as described herein, and demonstrate AGE-binding activity. The particular cysteine-bounded loop domain is a common 17–18 residue hydrophilic loop ($CX_{15-16}C$) which has been named herein an AGE-binding cysteine-bounded loop domain or "ABCD" motif. The immediate utility of this structure is in the measurement of AGE levels in tissues and body fluids and the treatment of conditions characterized by aberrant AGE presence and activity generally and specifically, in relation to bacterial infection.

Therapeutic uses of the binding motif, active fragments thereof and cognate molecules extend to the direct treatment of patients to overcome bacterial infection by assisting the action of antibacterial proteins such as lysozyme and lactoferrin. The same agents could be used in an extracorporeal fashion, such as in a suitable device using, for example, selectively permeable "dialyzing" membrane, to sequester and remove AGE peptides and AGE proteins from blood or serum. Blood supplies could be treated in this fashion to reduce AGE levels and to thereby further reduce the likelihood of infection by reducing the development of in vivo protein/tissue senescence. The agents of the present invention could function to opsonize AGE peptides and in this way assist in their in vivo clearance by the body's mechanisms.

The AGE-binding motif of the present invention, including active fragments thereof and cognate molecules, may also be used in diagnostic assays including drug discovery assays, to identify other active agents that could act as modulators of AGE activity and presence. Devices are contemplated that would contain such agents and that could bind to and thereby sequester AGE proteins and peptides to remove them from the body. Other diagnostic uses contemplate the use of the binding motif as a binding partner in the same manner as an anti-AGE antibody, for the capture of AGE-modified proteins, peptides, and other biomolecules, as an adjunct in an imaging assay for AGE-containing plaques such as those found in patients suffering from Alzheimers disease or atherosclerosis. In this latter utility, molecules bearing the binding motif or an active fragment thereof would be able to localize to amyloid and like plaques and likewise to other regions of AGE accumulation, and thereby assist in their measurement. These applications will best be realized when the AGE-targeting function of the ABCD peptide, an active fragment thereof or a cognate molecule or congener which by molecular resemblance shares AGE-binding activity with the ABCD peptide is conjugated to a label or tag that facilitates detection of the AGE-target conjugates.

The binding affinity of the agents of the present invention could be put to a variety of nontherapeutic uses, including their incorporation into personal care and cosmetic products that capitalize on the binding to topically resident AGEs. Thus, skin colorants, mascara and tooth whitening agents may be prepared which are based on the attachment to the agents of the invention of the appropriate visual indicator or colorant.

Accordingly, it is a principal object of the invention to provide a binding motif for that is specific to proteins or other biomolecules that have undergone advanced glycosylation.

It is a further object of the present invention to provide agents comprising or containing the binding motif as aforesaid, that exhibit a broad scope of utility including diagnostic, therapeutic and cosmetic applications.

It is a still further object of the present invention to provide methods for reversing AGE-mediated inhibition of antibacterial proteins.

It is a yet further object of the present invention to provide a method as aforesaid which is characterized by the discovery and use of the binding affinity of lysozyme and lactoferrin for advanced glycosylation endproducts.

Yet a further object of the present invention is to provide a method for treating AGE complications by administering a molecule having the structure of a hydrophilic cysteine loop such as that found in lysozyme and lactoferrin to inactivate AGEs.

Yet a further object is to provide a method for treating pathologies in which the presence and activity of AGEs is implicated by administering a molecule or active fragment thereof having the structure of the hydrophilic cysteine loop such as that found in lysozyme and lactoferrin, including lysozyme or lactoferrin, to assist in the removal of the AGEs.

Accordingly, still a further object of the invention is to provide pharmaceutical compositions comprising such a molecule having the structure of the hydrophilic cysteine loop such as that found in lysozyme and lactoferrin.

Other objects and advantages will become apparent to those skilled in the art from a review of the ensuing description which proceeds with reference to the following illustrative drawings.

DETAILED DESCRIPTION OF THE INVENTION

Figure 1A:
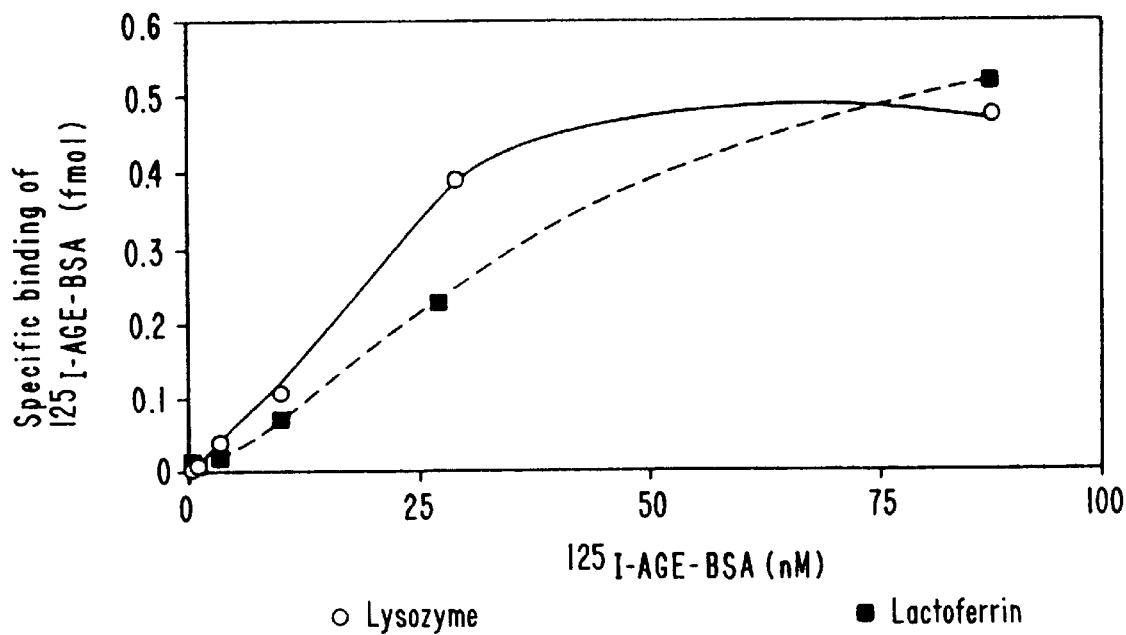
FIG. 1 demonstrates the binding of AGE-BSA to lysozyme and lactoferrin. AGE-BSA was prepared and radiolabeled as previously described (Vlassara et al., 1986, J. Exp. Med. 164: 1301). Hen egg-white lysozyme and purified human lactoferrin (Sigma) were immobilized on nitrocellulose membrane at 3 $\mu$g/dot. The membrane was blocked with 1% BSA in binding and washing buffer (0.05% Tween-20, 1×PBS), and blotted with 1,000,000 cpm $^{125}$I-AGE-BSA/dot (NEN, specificity: 2000 cpm/ng BSA). After wash, bound $^{125}$I-AGE-BSA was determined by a $\gamma$-counter. A. Saturation curve of AGE-BSA binding to lysozyme and lactoferrin. The $K_d$ determined by Scatchard analysis for lysozyme and lactoferrin are 5 and 30×10$^{-8}$M, respectively. Results are representative of at least three independent experiments. B. Competition of AGE binding to LZ or LF with BSA, AGE-BSA, AGE-ovalbumin, FFI-B, Glucosamine, heparin, fucoidan, keratan, chondroitin and polyglutamic acid (at approximately 50-fold concentration).

The present invention is directed to the discovery that a binding motif specific to advanced glycosylation endproducts (AGEs) exists, and correspondingly, extends to diagnostic and therapeutic uses to which the discovery may be put. More specifically, certain antibacterial proteins comprising this domain and others, in particular lysozyme and lactoferrin, bind to advanced glycosylation endproducts (AGEs) with high affinity, and this binding has been observed to be substantially incompatible with the antibacterial properties of these proteins. Accordingly, the invention relates to methods for treating diseases and disorders associated with increased levels of AGEs, and compositions for the same. The invention is also directed to methods for determining a prognosis of AGE complications in a patient suffering from an AGE-associated disease or disorder, directly by measuring AGEs, or indirectly by measuring the level of activity of antibacterial proteins, such as lysozyme and lactoferrin, in a biological sample from a subject. While not intending to be limited by any particular theory or hypothesis, it is believed that higher levels AGEs inhibit the activity of such antibacterial proteins, thus rendering an individual more susceptible to bacterial infection.

The following terms are defined to the extent that they may appear herein.

The term "a molecule having a hydrophilic cysteine-bounded loop domain", "a hydrophilic loop domain", or "motif", or other syntactic variants, refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D or L optical isomers, and amino acid analogs and peptidomimetics. The molecule of the invention is constructed to have a structure corresponding to $R_1Xaa_1Xaa_nXaa_2R_2$. $Xaa_1$ and $Xaa_2$ are amino acids capable of forming a cross link, such as cysteine or glutamic acid or aspartic acid and lysine. In particular, where $Xaa_1$ and $Xaa_2$ are each cysteine, the cysteine residues form or are capable of forming a disulfide bond. $R_1$ and $R_2$ are independently a polypeptide, a $C_1$ to $C_{12}$ alkyl, aryl, heteroalkyl, or heteroaryl group, or hydrogen. $Xaa_n$ is any L- or D-amino acid; and n=13–18. In specific embodiments, infra, the molecule is a polypeptide having 17 or 18 L-amino acids (including the cysteine residues designated Xaa and $Xaa_2$).

The term "antibacterial protein" as used herein refers to a protein that has bacteriocidal activities, e.g., lysozyme and lactoferrin, and that contains a hydrophilic cysteine loop of from about 15 to about 20 amino acid residues, including the cysteines that form cystine and that bracket the other 13–18 residues. Other examples of antibacterial proteins of the invention include, but are not limited to, defensins, azurocidins, neutrophil antibiotics, and seroprocidins. Such proteins can be from any animal species, e.g., mammalian (human, bovine, ovine, equine, caprine, porcine, canine, feline, murine, rat, etc.), avian (chicken, etc.), or other sources.

The term "hydrophilic" in conjunction with the molecule as defined above means that the overall character of the molecule is polar, and the molecule is water soluble. This results from inclusion of subunits of the molecule, e.g., amino acid residues, with polar functional groups. For example, in the instance where the molecule is a polypeptide, choices for amino acid residues include those with cationic side chains (arginine and lysine), anionic side chains (aspartate and glutamate), and neutral polar side chains (asparagine, glutamine, serine, and threonine) (see, e.g., Cantor and Schimmel, in BIOPHYSICAL CHEMISTRY Part I. The Conformation of Biological Macromolecules, W. H. Freeman and Company: San Francisco, 1980, pp. 41–53).

As used herein, the term "AGE-" refers to the compound which it modifies as the reaction product of either an advanced glycosylation endproduct or a compound which forms AGEs and the compound so modified, such as the bovine serum albumin (BSA). Thus, AGEs include, but are not limited to, AGE-proteins (such as BSA-AGE), AGE-lipids, AGE-peptides, and AGE-DNA. AGE-polypeptides or AGE-proteins can be formed in vitro or in vivo by reacting a polypeptide or protein with an AGE, such as an AGE-peptide, or with a compound such as a reducing sugar, e.g., glucose, until the polypeptide or protein is modified to form the AGE-polypeptide or AGE-protein.

The term "glycosylation" is used herein to refer to the non-enzymatic reaction of reducing sugars with a nucleophile, in particular an amine group, on a polypeptide or protein, such as hemoglobin, a lipid, or DNA, which leads to formation of AGEs. These processes are well known in the art, as described above. Recently, the term "glycation" has become more favored to refer to non-enzymatic glycosylation processes. Thus, the term "glycosylation," as specifically defined herein, and "glycation" are equivalent.

A composition comprising "A" (where "A" is a single protein, cell, etc.) is substantially free of "B" (where "B" comprises one or more contaminating proteins, cells, etc.) when at least about 75% by weight of the proteins (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness, and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically acceptable carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solutions, such as saline solutions and aqueous dextrose and glycerol solutions, are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

As stated above, the present invention is based, in part, on the discovery that lysozyme and lactoferrin, major endogenous antibacterial proteins, bind to glucose-modified proteins (AGEs) with high affinity. The invention is further based on the observation that AGE binding inhibits the enzymatic and bactericidal activity of lysozyme, and blocks or reverses the bacterial agglutination and bacterial killing induced by lactoferrin.

The invention is further based on the discovery that a conserved domain present in both lysozyme and lactoferrin, as well as other antibacterial proteins, mediates binding to AGE. This domain contains a common 17–18 amino acid hydrophilic cysteine loop structure. Cysteine-bounded loops corresponding the lysozyme and lactoferrin were prepared synthetically, and these peptides demonstrated AGE-binding activity.

These data indicate that molecules containing the structure of a hydrophilic cysteine-bounded loop, preferably of 17–18 amino acids, can be used to inhibit AGE-mediated inactivation of antibacterial proteins that contain such hydrophilic cysteine loops. Furthermore, such molecules may be used to detect the presence of AGEs in a sample, to target various labels to AGE-modified molecules or tissues, to partition AGEs out of a sample (e.g., during dialysis), and to block the cross-linking activity of AGES.

In particular it has been found that lysozyme binds to glucose-modified proteins, i.e. thouse bearing advanced glycosylation endproducts (AGEs), with a high affinity. AGE-BSA inhibits the enzymatic and bactericidal activity of lysozyme and blocks or reverses the bacterial agglutination and bacterial killing induced by AGE-binding lactoferrin. Mapping by proteolytic digestion revealed a single AGE-binding domain in lysozyme and two AGE-binding domains in lactoferrin. Within these domains, a common 17–18 amino acid hydrophilic cysteine loop ($CX_{15-16}C$) was found, that has been named AGE-binding cysteine-bounded domain or "ABCD" motif. Synthetic cysteine-bounded loop domains of lysozyme and lactoferrin did exhibit AGE-binding activity. Similar loops are also present in other members of antimicrobial proteins.

As set forth later herein, it is postulated that elevated levels of AGEs in tissues and sera of diabetic patients inhibit endogenous antibacterial proteins by binding to this conserved motif, and thereby increase the susceptibility to bacterial infections.

To provide a more complete understanding of the invention, the specification is divided into these various aspects of the invention, and sections relating to therapeutics and diagnostics.

Molecules Containing a Hydropbilic Loop Domain

According to the present invention, a molecule having a hydrophilic loop structural domain, which molecule binds to AGEs, can be prepared and used. In specific embodiments, infra, polypeptides having the amino acid sequences depicted in FIG. 5A (SEQ ID NO:7, SEQ ID NO:8 and SEQ ID NO:9) have been prepared. These polypeptides are observed experimentally to bind to AGEs. Peptides or peptide analogs (i.e., molecules containing non-peptidyl bonds, non-naturally occurring amino acids, and the like, but that have similar structural, physical, and chemical properties of peptides) can be prepared synthetically, e.g., using the well known and highly developed solid phase condensation chemistry. Accordingly, the molecule can be prepared from L- or D-amino acids, polyesters and polyethers, amino acid analogs, non-classical amino acids, peptidomimetics, and the like (see Lam et al., International Patent Publication No. WO 92/00252, which is specifically incorporated herein by reference).

The invention extends to other hydrophilic polypeptide loop domains, e.g., loops formed with disulfide, lactam, lactone or other ring closing moieties. That is, the spacer hydrophilic subunits of such a molecule are bracketed with a subunit, e.g., an amino acid, that provides a chemical functional group capable of crosslinking to cyclize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, lysine and glutamic acid or aspartic acid to form an $\epsilon$-amino/$\gamma$- (or $\beta$-)acid amide, and a chelator such as $\gamma$-carboxyl-glutamic acid (Gla) (Bachem) to chelate a transition metal and form a cross-link. Protected $\gamma$-carboxyl glutamic acid may be prepared by modifying the synthesis described by Zee-Cheng and Olson (1980, Biophys. Biochem. Res. Commun. 94: 1128–1132). A peptide in which the peptide sequence comprises two amino acids capable of crosslinking may be treated, e.g., by oxidation of cysteine residues to form a disulfide (cystine) or addition of a metal ion to form a chelate, so as to crosslink and cyclize the peptide to form the hydrophilic loop.

Based on the peptides identified herein that bind to AGEs, the general structural motif of a molecule of the invention can be determined. Identification and screening of antagonists is further facilitated by determining structural features of the protein, e.g., using X-ray crystallography, neutron diffraction, nuclear magnetic resonance spectrometry, and other techniques for structure determination. The structure of the hydrophilic cysteine loop domain of the invention can be analyzed by various methods known in the art. Structural analysis can be performed in part by identifying sequence similarity with other known proteins. The degree of similarity (or homology) can provide a basis for predicting structure and function of the loop.

For example, sequence comparisons can be performed with sequences found in GenBank, using, for example, the FASTA and FASTP programs (Pearson and Lipman, 1988, Proc. Natl. Acad. Sci. USA 85: 2444–48). As has been performed herein, a candidate polypeptide for a hydrophilic cysteine loop structure should be further characterized by a hydrophilicity analysis (e.g., Hopp and Woods, 1981, Proc. Natl. Acad. Sci. U.S.A. 78: 3824). A hydrophilicity profile can be used to confirm that the sequence of the candidate polypeptide is hydrophilic. Manipulation, translation, and secondary structure prediction, as well as open reading frame prediction and plotting, can also be accomplished using computer software programs available in the art. The invention further envisions quantitative structural determination of the hydrophilic loop domain. Specifically, nuclear magnetic resonance (NMR), infrared (IR), Raman, and ultraviolet (UV), especially circular dichroism (CD), spectroscopic analysis can be used to characterize the structural motif of the hydrophilic loop. In particular NMR provides very powerful structural analysis of molecules in solution, which more closely approximates their native environment (Marion et al., 1983, Biochem. Biophys. Res. Comm. 113: 967–974; Bar et al., 1985, J. Magn. Reson. 65: 355–360; Kimura et al., 1980, Proc. Natl. Acad. Sci. U.S.A. 77: 1681–1685). Other methods of structural analysis can also be employed. These include but are not limited to X-ray crystallography (Engstom, A., 1974, Biochem. Exp. Biol. 11: 7–13). More preferably, co-crystals of the hydrophilic loop and an AGE can be studied. Analysis of co-crystals provides detailed information about binding, which in turn allows for rational design of analogs of the hydrophilic cysteine loops found in, e.g., lysozyme and lactoferrin. Computer modeling can also be used, especially in connection with NMR or X-ray methods (Fletterick, R. and Zoller, M. (eds.), 1986, Computer Graphics and Molecular Modeling, in *Current Communications in Molecular Biology,* Cold Spring Harbor Laboratory, Cold Spring Harbor, N.Y.).

Alternatively, a peptide or polypeptide molecule according to the invention, including lysozyme and lactoferrin, can be produced recombinantly. The polypeptide or protein may be expressed by a compatible cellular colony. Thus, in accordance with this aspect of the present invention there may be employed conventional molecular biology and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence. Many coding sequences for antibacterial proteins, in particular lysozyme, lactoferrin, defensins, azurocidin, neutrophil antibiotics, and seroprocidins are known in the art (Gabay et al., 1993, Opin. Immunol. 5: 97–102; Leher et al., 1993, Annu. Rev. Immunol. 11: 105–28).

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

Therapeutic Methods and Compositions

As the hydrophilic cysteine loop domain appears to play a role in the recognition, and may also be involved with removal, of advanced glycosylation endproducts in vivo, the present invention contemplates therapeutic applications for molecules having the structure of the hydrophilic cysteine loop domain, including active fragments, mimics thereof, and cognate or congener molecules thereto. Thus, a molecule of the invention that contains or comprises a hydrophilic loop structure can be prepared for administration in various scenarios for therapeutic purposes, in most instances to assist in reducing the antibiotic protein inhibitory activity, cross-linking activity, and even concentration, of AGEs in vivo.

Numerous therapeutic formulations are possible and the present invention contemplates all such variations within its scope. A variety of administrative techniques may be utilized, among them topical applications as in ointments, creams, gels, and lotions to be applied directly to a wound or sore, or on surgical and other topical appliances such as, surgical sponges, bandages, gauze pads, and the like. Such topical pharmaceutical compositions have particular use for the treatment of diabetic ulcers, where the antibacterial protein inhibitory activity of AGEs may be involved in delaying the healing process. Alternatively, such compositions may be administered by parenteral techniques such as subcutaneous, intravenous and intraperitoneal injections, catheterizations and the like.

Corresponding therapeutic utilities take advantage of the demonstrated activity of the present molecule containing a hydrophilic loop structure, active fragments, mimics, congeners, and cognates thereof, toward advanced glycosylation endproducts. Thus, to the extent that the in vivo recognition and removal of AGEs serves to treat ailments attributable to their presence in an excess concentration, the administration of the present molecule comprises an effective therapeutic method. In particular, the present molecules could serve to localize concentrations of AGE accumulation and to enhance their detection and removal. Such conditions as atherosclerosis with or without diabetes, diabetic nephropathy, renal failure and the like may be treated and/or averted by the practice of the therapeutic methods of the present invention. A specific strategy involves the ability of the present molecules to opsonize AGE peptides and to thereby facilitate their in vivo clearance and removal.

Average quantities of the active agent effective for a positive therapeutic outcome may vary between different individuals, and in particular should be based upon the recommendations and prescription of a qualified physician or veterinarian, with an exemplary dosage regimen extending to up to about 25 mg/kg/day.

The molecule having a hydrophilic loop domain, fragments, mimics, congeners, and cognates thereof, may be prepared in a therapeutically effective concentration as a pharmaceutical composition with a pharmaceutically acceptable carrier, as defined above. Preferably, as noted above, the carrier is suitable for topical administration. Other compatible pharmaceutical agents may possibly be included, so that for example certain agents may be simultaneously co-administered. In a preferred aspect, an inhibitor of AGE-formation is administered with the molecule, so as to simultaneously induce removal of AGEs and inhibit formation of new AGEs.

Thus, the invention provides for administering a molecule having a hydrophilic loop domain and an agent that blocks the post-glycosylation step, i.e., the formation of fluorescent or crosslinking chromophores whose presence is associated with, and leads to, the adverse sequelae of glycosylation. An ideal agent would prevent the formation of a chromophore and its associated cross-links of proteins to proteins and trapping of proteins on to other proteins. The ideal agent would prevent or inhibit the long-term, glycosylation reactions that lead to the formation of the late-stage advanced glycosylation end products that are a direct cause of AGE-associated pathology.

An inhibitor of the formation of AGEs includes compounds that react with a carbonyl moiety of an early glycosylation product. Representative of such advanced glycosylation inhibitors are aminoguanidine, lysine and α-hydrazinohistidine. In a specific embodiment, the inhibitor is aminoguanidine (AG) and derivatives thereof. Pharmaceutical compositions and methods involving AG and derivatives thereof are well known, as described in U.S. Pat. Nos. 4,758,583, issued Jul. 19, 1988; No. 4,908,446, issued Mar. 13, 1990; No. 4,983,604, issued Jan. 8, 1991; No. 5,100,919, issued Mar. 31, 1992; No. 5,106,877, issued Apr. 21, 1992; No. 5,114,943, issued May 19, 1992; No. 5,128,360, issued Jul. 7, 1992; No. 5,130,324, issued Jul. 14, 1992; No. 5,130,337, issued Jul. 14, 1992; No. 5,137,916, issued Aug. 11, 1992; No. 5,140,048, issued Aug. 18, 1992; No. 5,175,192, issued Dec. 29, 1992; No. 5,218,001, issued Jun. 8, 1993; No. 5,221,683, issued Jun. 22, 1993; No. 5,238,963, issued Aug. 24, 1993; No. 5,243,071, issued Sep. 7, 1993; and No. 5,254,593, issued Oct. 19, 1993. Other inhibitors of AGE formation are described in U.S. Pat. No. 5,258,381 issued Nov. 2, 1993, U.S. Pat. No. 5,356,895 issued Oct. 18, 1994. U.S. Pat. No. 5,272,176 issued Dec. 21, 1993 U.S. Pat. No. 5,318,982 issued Jun. 7, 1994 U.S. Pat. No. 5,358,960 issued Oct. 25, 1994, and U.S. Pat. No. 5,534,540 issued Jul. 9, 1996. Each of the foregoing patents and patent applications is specifically incorporated herein by reference in its entirety.

Another important aspect of the invention is use of a molecule having a hydrophilic loop domain, fragments, mimics, congeners, and cognates thereof, to partition AGEs from in vivo samples and thus remove the toxic AGEs. That is, a molecule of the invention can be used, e.g., in dialysis, to clear AGEs from the blood. A particular advantage of the invention is that where such a molecule also has antibacterial properties, e.g., lysozyme or lactoferrin, it inherently contributes antiseptic characteristics to a dialysis procedure. Thus, in one embodiment, the molecule of the invention is immobilized on a membrane, e.g., a dialysis membrane, to bind to and remove AGEs from the blood.

In another embodiment, the invention provides a device for adsorbing AGEs from a biological sample. The device comprises a closed structure, which structure is fabricated of an AGE-permeable membrane. Disposed within such device are particles to which a molecule of the invention is irreversibly associated or immobilized. In a specific embodiment, a "tea-bag" arrangement is envisioned, wherein the device forms the tea-bag and contains particles capable of binding to AGEs. A similar device formed of polypropylene mesh is described in Houghten, 1985, Proc. Natl. Acad. Sci. USA 82: 5131–35; and U.S. Pat. No. 4,631,211. Such a device can be used ex vivo or implanted in vivo in a subject for whom removal of AGEs is desired.

Diagnostic Methods

In one aspect, the invention relates to detection of the level of bacteriocidal activity of endogenous antibacterial proteins in a subject, preferably a human, believed to be suffering from elevated levels of AGEs, and complications derivative thereof. In particular, a sample from such an individual can be tested for lysozyme or lactoferrin activity, or both. A decrease in the level of antibacterial activity compared to the individual at an earlier time or a normal individual may be indicative of inhibition of the antibacterial proteins by AGEs. Such a diagnosis may be confirmed indirectly by detecting elevated levels of AGEs. A decrease in the level of endogenous antibacterial protein bacteriocidal activity is prognostic of greater susceptibility to bacterial infections.

Suitable samples for detection of the level of bacteriocidal activity of antibacterial proteins can be selected from saliva, mucous (e.g., nasal and pulmonary), phlegm, wound exudate, and infected sore exudate, as well as blood, plasma, urine, cerebrospinal fluid, lymphatic fluid, and tissue.

Ligands capable of binding to antibacterial proteins according to the invention include, but are not limited to, AGE-BSA and OVA-AGE, prepared as described infra, and the compounds FFI and AFGP, individually and bound to carrier proteins such as the protein albumin. A carrier may be selected from the group consisting of carbohydrates, proteins, synthetic polypeptides, lipids, bio-compatible natural and synthetic resins, antigens and mixtures thereof.

The present invention seeks to diagnose or determine a prognosis of AGE-related complications, monitoring the course of progression or treatment of an AGE-associated disease or disorder, or monitor a therapy for an AGE-associated disease or disorder. Such conditions as age- or diabetes-related hardening of the arteries, skin wrinkling, arterial blockage, and diabetic, retinal and renal damage in animals all result from the excessive buildup or trapping that occurs as advanced glycosylation endproducts increase in quantity. Therefore, the diagnostic method of the present invention seeks to avert pathologies caused at least in part by the accumulation of advanced glycosylation endproducts in the body by monitoring the amount level of antibacterial protein bacteriocidal activity.

In yet another embodiment, the molecule of the invention can be used to detect the presence or level of AGEs in a sample, e.g., as an adjunct to or in place of an anti-AGE antibody as described in Bucala, U.S. patent application Ser. No. 07/956,849, filed Oct. 1, 1992, entitled "IMMUNOCHEMICAL DETECTION OF IN VIVO ADVANCED GLYCOSYLATION ENDPRODUCTS," which is specifically incorporated herein by reference in its entirety.

Thus, both the molecule having a hydrophilic loop domain, fragments, mimics, congeners, and cognates thereof, and any binding partners thereto that may be prepared, are capable of use in connection with various diagnostic techniques, including immunoassays, such as a radioimmunoassay, using for example, a receptor or other ligand to an AGE that may either be unlabeled or if labeled, then by either radioactive addition, reduction with sodium borohydride, or radioiodination. These general procedures and their application are all familiar to those skilled in the art and are presented herein as illustrative and not restrictive of procedures that may be utilized within the scope of the present invention. The "competitive" procedure, Procedure A, is described in U.S. Pat. Nos. 3,654,090 and 3,850,752. Optional procedure C, the "sandwich" procedure, is described in U.S. Pat. Nos. RE 31,006 and 4,016,043, while optional procedure D is known as the "double antibody", or "DASP", procedure.

Various assay formats are also contemplated by the present invention for detecting the presence, and if desired, the amount, of AGEs using the molecule of the invention. For example, a direct "sandwich"-type ELISA can be performed. Blotting formats, in which all the proteins from a sample are blotted, e.g., by electroblotting, on a solid support, such as nitrocellulose, for detecting the presence, and if desired, the amount of AGEs are also contemplated by the instant invention. In a specific embodiment, infra, after blotting the hydrophilic loop-containing peptides in a sample on nitrocellulose, AGE is detected using a labeled AGE.

The present invention includes assay systems that may be prepared in the form of test kits for the quantitative analysis of the extent of the presence of advanced glycosylation endproducts. The system or test kit may comprise a labeled component prepared by one of the radioactive and/or enzymatic techniques discussed herein, such as an antibody or ligand, as listed herein; and one or more additional immunochemical reagents, at least one of which is capable either of binding with the labeled component, its binding partner, one of the components to be determined or their binding partner(s).

In a further embodiment of this invention, commercial test kits suitable for use by a medical specialist may be prepared to determine the presence or absence of AGEs. Such kits can also be used to determine the amount of AGEs in a sample. In accordance with the testing techniques discussed above, one class of such kits will contain at least labeled molecule having a hydrophilic loop domain, fragment, mimic, congener, or cognate thereof, and may include directions, depending upon the method selected, e.g., "competitive", "sandwich", "DASP" and the like. The kits may also contain peripheral reagents such as buffers, stabilizers, etc.

Accordingly, a test kit may be prepared for the demonstration of the presence and activity of AGE comprising:

(a) a predetermined amount of at least one labeled chemically reactive component obtained by the direct or indirect attachment of a molecule having a hydrophilic loop domain to a detectable label, fragments, mimics and cognates thereof;
(b) other reagents; and
(c) directions for use of said kit.

All of the protocols disclosed herein may be applied to the qualitative and quantitative determination of AGEs and to the concomitant diagnosis and surveillance of pathologies in which the accretion of advanced glycosylation endproducts is implicated. Such conditions as diabetes and the conditions associated with aging, such as atherosclerosis and skin wrinkling represent non-limiting examples, and accordingly methods for diagnosing and monitoring these conditions are included within the scope of the present invention.

The diagnostic uses of the molecules of the present invention extend to their use as part of drug discovery assays to identify agents that could serve in a like capacity. For example, the molecules may be used as a binding partner in the same manner as an anti-AGE antibody, for the capture of AGE-modified proteins and peptides, and as an adjunct in an imaging assay for AGE-containing plaques such as those found in patients suffering from Alzheimers disease and scrapie.

The invention contemplates a variety of uses not strictly diagnostic or therapeutic in purpose. For example, the affinity of the present molecules for AGEs commends their use in the formulation of personal care and cosmetic preparations that would contain the present molecule(s) having attached thereto a colorant or the like. Such preparations could be used for facial and eye make-up, face or body tan simulating solutions, and as tooth whiteners.

The present invention will be better understood from a consideration of the following illustrative examples and data.

EXAMPLE 1

The mechanism of diabetes-associated high susceptibility of infections remains unknown. Lysozyme and lactoferrin are two major non-homologous endogenous antibacterial proteins present in saliva, nasal secretion, mucus, and lysosomes of neutrophils and macrophages (Philips, Sci. Am. 215: 78; Anderson et al., 1992, Nature 344: 784; Reiter et al., 1969, Nature 216: 643; Tenovu et al., 1991, Proc. Finn. Dent. Sco. 87: 197). We hypothesize that elevated levels of AGE may mediate the suppression of certain normal host defense mechanisms in diabetic patients. The following example illustrates the ability of lysozyme and lactoferrin to bind to BSA-AGE in a time-dependent manner thus providing a likely means to reverse the AGE-mediated inhibition of antibacterial proteins.

Figure 1B:
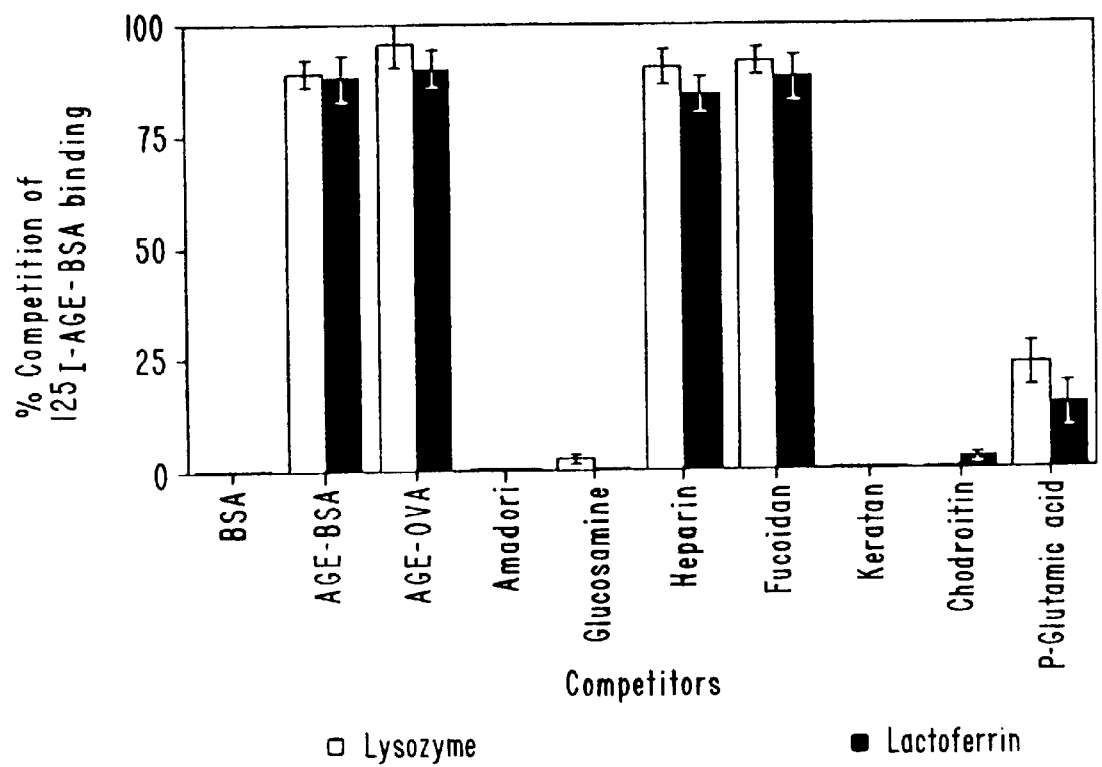

Using $^{125}I$ labeled glucose modified bovine serum albumin (AGE-BSA) as a probe, we found that chicken lysozyme and recombinant human lysozyme exhibit AGE-specific binding activity on Western ligand blot (FIG. 1). Human lactoferrin, similar to bovine lactoferrin reported earlier (Shmid et al., 1992, J. Bio. Chem. 267: 14987), also binds to AGE-BSA. At 4° C., the binding of AGE-BSA to both lysozyme and lactoferrin is apparently time-dependent and reaches a plateau by 30 minutes (FIG. 1A). The binding is also saturable with an increasing concentration of $^{125}I$-AGE-BSA ligand (FIG. 1A). The calculated disassociation constant (Kd) is $5 \times 10^{-8}M$ for lysozyme and $25 \times 10^{-8}M$ for lactoferrin. This binding between AGE-BSA and lysozyme or lactoferrin is an AGE-specific non-covalent interaction since binding can be competed with other AGE-modified proteins, but not by non-glycated carrier proteins, glucose, Amadori products, glucosamine, or polyanionic/polycationic molecules (FIG. 1B).

Figure 2A:
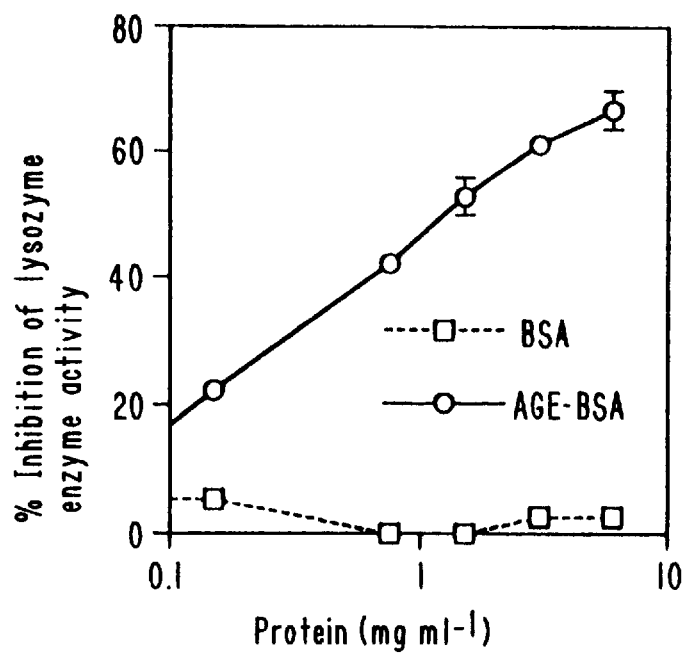
FIG. 2 shows that AGE-BSA inhibits the antibacterial activities of lysozyme and lactoferrin. A. Inhibition of lysozyme enzymatic activity by AGE-BSA. Enzymatic activity of recombinant human lysozyme (Sigma) with different amount of AGE-BSA were determined by measuring the lysis of lyophilized *Micrococcus lysodeikticus* (ATCC 4698) with a turbidimetric assay under recommended conditions (Sigma). Lysozyme (4 $\mu$g/ml) was added to 1 ml substrate (0.015% *Micrococcus* suspension in 66 mM $K_2SO_4$ buffer, pH 6.24) with or without addition of AGE-BSA or BSA at indicated concentrations and the $A_{420}$ was determined by kinetic analysis. Data at log phase (3 minutes) are presented here. Similar results were observed at other time points. B. AGE-BSA abrogates bacterial agglutination induced by lactoferrin. Lactoferrin (150 $\mu$g), lactoferrin plus AGE-BSA (150 $\mu$g), or lactoferrin plus BSA (150 $\mu$g) were added to 1 ml of *Micrococcus* suspension (0.015%), and the agglutination was determined by immediate measurement of turbidity change at $OD_{700}$. AGE-BSA was also added to lactoferrin-agglutinated bacterial suspension to observe the reversal of agglutination. C and D. AGE-BSA inhibition of bactericidal activity of lysozyme and lactoferrin. Live *Micrococcus luteus* (ATCC 9341) at 2.5×10$^{-5}$ CFU/ml in Nutrient Broth (DIFCO) were incubated with lysozyme or lactoferrin plus AGE-BSA, AGE-ovalbumin, or BSA at indicated concentrations. The minimal inhibitory concentrations (MIC) at these conditions were determined by visualized bacterial growth after 18 hours incubation at 30° C.
Figure 2B:
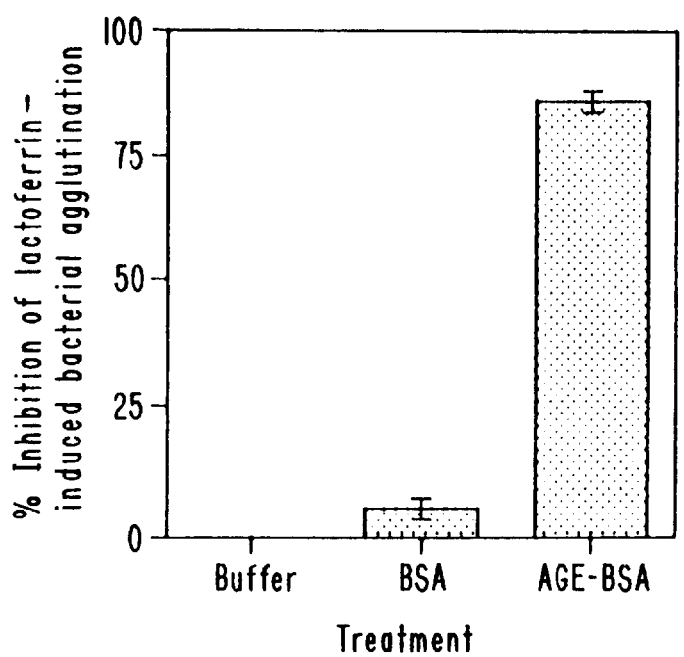
Figure 2C:
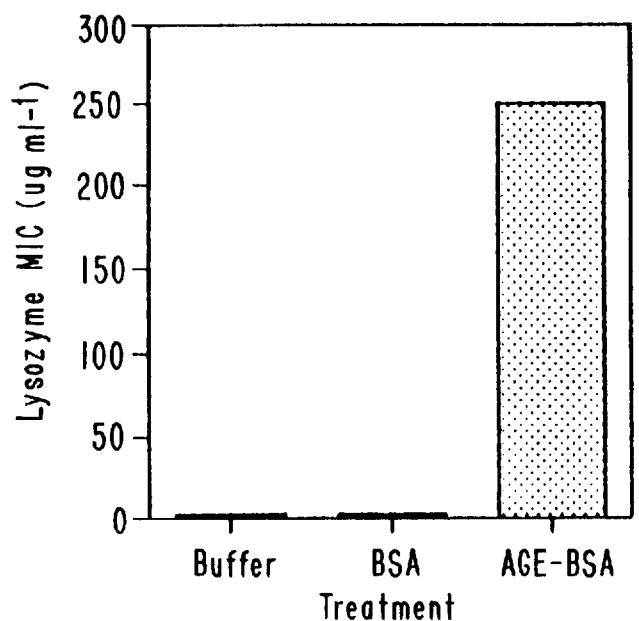
Figure 2D:
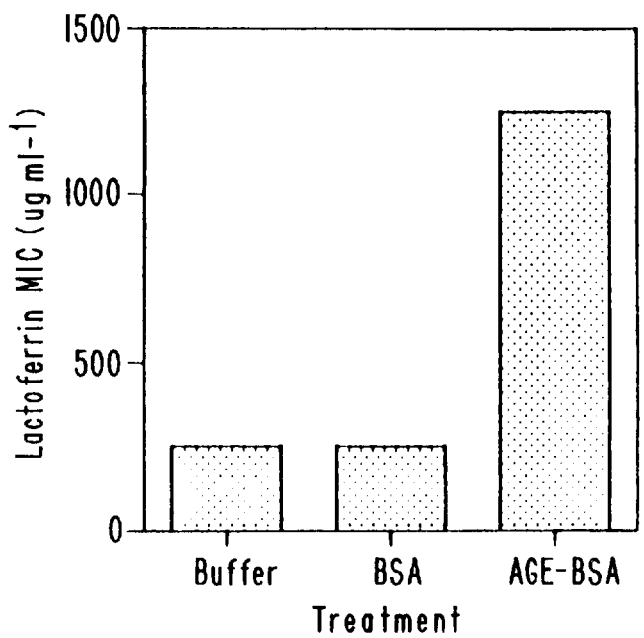

Lysozyme lyses Gram positive and some Gram negative bacteria by specific cleavage of 1–4 β linkage between N-acetylglucosamine and N-acetylmurimate which comprise the peptidoglycan backbone of the bacterial cell wall (Philips, 196B, Sci. Am. 215: 78). By using lyophilized *Micrococcus lysodeikticus* as a substrate, we found that AGE-BSA inhibited the enzymatic activity of recombinant human and chicken lysozyme in a dose-dependent manner (FIG. 2A), whereas, non-AGE-modified BSA control did not alter the activity of lysozyme. However, this inhibition did not reach 100% with an increasing dose of AGE-BSA suggesting AGE may be an indirect competitor for the substrate of lysozyme. Similarly, human lactoferrin-induced agglutination of *Micrococcus lysodeikticus* (Soukka et al., 1993, Archs Oral Biol. 38: 227) was completed blocked or reversed by addition of AGE-BSA, but not by BSA (FIG. 2B). The bactericidal activity of both lysozyme and lactoferrin was also inhibited by AGE-BSA as indicated by changing of minimal inhibition concentrations,(MIC) of both proteins in the presence of AGE-modified protein (FIGS. 2C,D). The addition of AGE-BSA or AGE-ovalbumin increased lysozyme MIC for Micrococcus by 125-fold. By titration of AGE-ovalbumin and lysozyme concentrations, the minimal inhibition molar ratio of AGE-ovalbumin over lysozyme was determined as 3:1. The foregoing data suggest the prognostic capability of the invention, as elevations in AGE correlate with increased risk of AGE-related conditions, and such elevations were and may be measured by the corresponding inhibition or inactivation of lysozyme and lactoferrin.

Figure 3C:
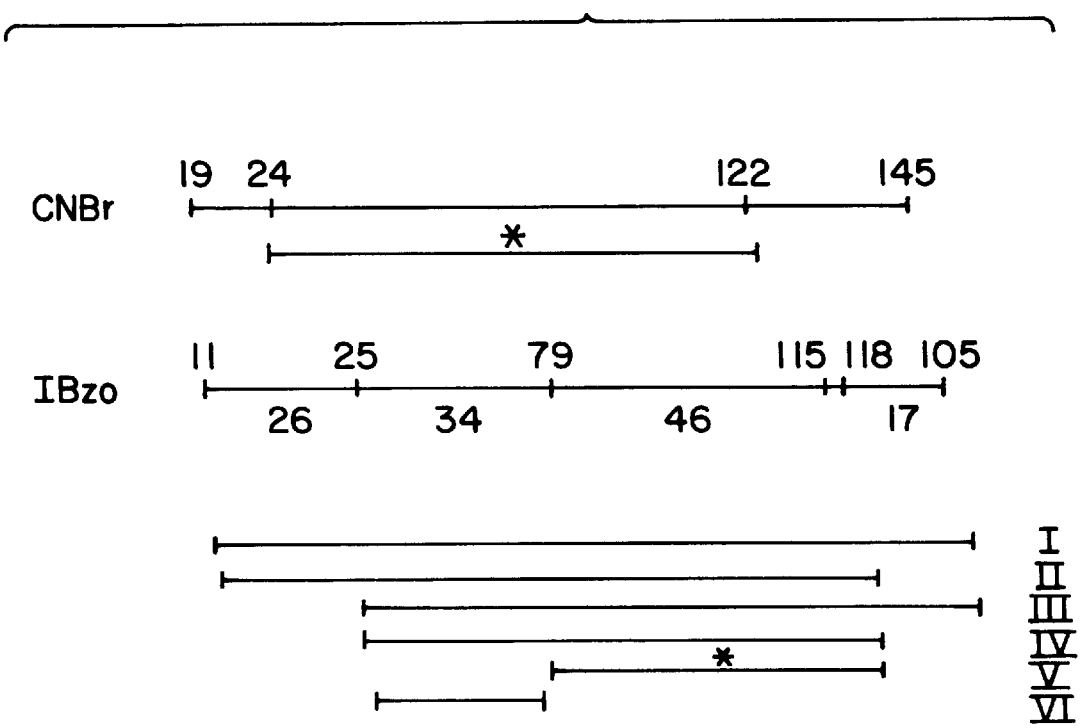
FIG. 3 presents a map of lysozyme AGE-binding domains. Lysozyme was digested with cyanogen bromide (CnBr) or idosobenzonate (IBzo) as previously described (Mahoney et al., 1979, Biochemistry 18: 38100). Digested peptides and intact proteins were diluted in reducing sample buffer and analyzed by SDS-PAGE over 15% or 25% gels, transferred onto nitrocellulose membranes which were then blocked with 1% BSA and probed with $^{125}$I-AGE-BSA. Amido black-stained nitrocellulose membranes, autoradiographs of ligand blots, and predicted digestion maps are presented. A. Lysozyme digested with CnBr. B. Lysozyme digested with IBzo. C. The predicted digestion maps and AGE-binding domains.

Although lysozyme and lactoferrin share bactericidal and AGE-binding activity, no apparent primary sequence homology exists between these two proteins. We mapped the AGE-binding domain in these two proteins by proteolytic digestion using cyanogen bromide (CnBr), V8 protease, or iodosobenzonate (IBzo). Digested peptides were electrophoresed through SDS-PAGE, transferred onto nitrocellulose membranes, and blotted with $^{125}$I-AGE-BSA. Partial CnBr digestion of chicken lysozyme indicated neither the first 12 residues at the N-terminal nor the last 25 residues at the C-terminal are required for AGE binding (FIG. 3A). Partial digestion with IBzo revealed that the smallest fragment, at ~3 kDa, does not have AGE-binding activity whereas the secondary smallest fragment, at ~5 kDa, still retains full AGE-specific binding activity (FIG. 3B). Based on the specific digestion map of lysozyme by CnBr and IBzo, the AGE-binding domain is localized to a 4.6 kDa fragment from amino acid 62 to 105 (FIG. 3C).

Figure 4A:
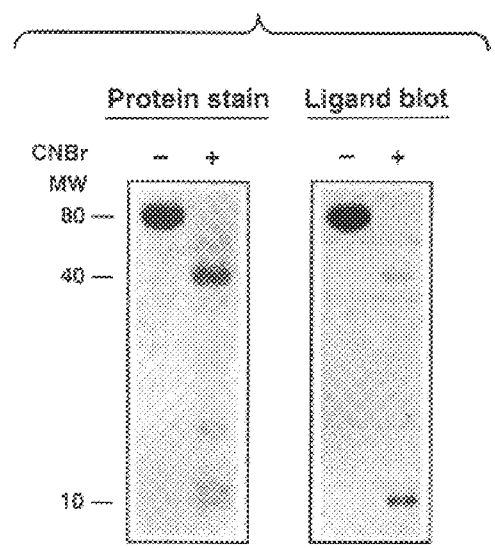
FIG. 4 shows a map of lactoferrin AGE-binding domains. Digestion of lactoferrin was performed as described in FIG. 3 for lysozyme (Mahoney et al., supra). Amido black-stained nitrocellulose membranes, autoradiographs of ligand blots, and predicted digestion maps are presented. A. Lactoferrin digested with CnBr. B. Lactoferrin digested with V8 Protease. C. The predicted digestion maps and AGE-binding domains.
Figure 4B:
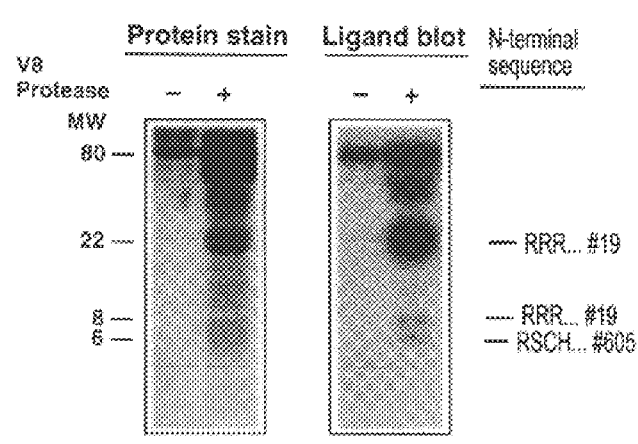

In contrast, digestion of human lactoferrin with CnBr resulted in both a 40 and a 10 kDa AGE-binding fragment (FIG. 4A). Partial digestion of lactoferrin with V8 protease revealed three distinct AGE-binding fragments of 22, 8, and 6 kDa (FIG. 4B). We have sequenced the N-terminal twenty amino acids of these three AGE-binding peptides and found that the 8 kDa peptide is localized at the N-lobe (a.a. #1–20) and the 6 kDa fragment is localized at the C-lobe (a.a. #605–625) of human lactoferrin. Additionally the 22 KDa peptide shares the same N-terminus with the 8 kDa fragment. CnBr and V8 protease digestion map and AGE-binding results are summarized in FIGS. 3A–C, and we concluded that there are at least two domains in lactoferrin (8 kDa, a.a. #1–80; 5 kDa, a.a. #603–653) that exhibit AGE-binding activity (FIG. 4C).

Figures 5A, 5B:
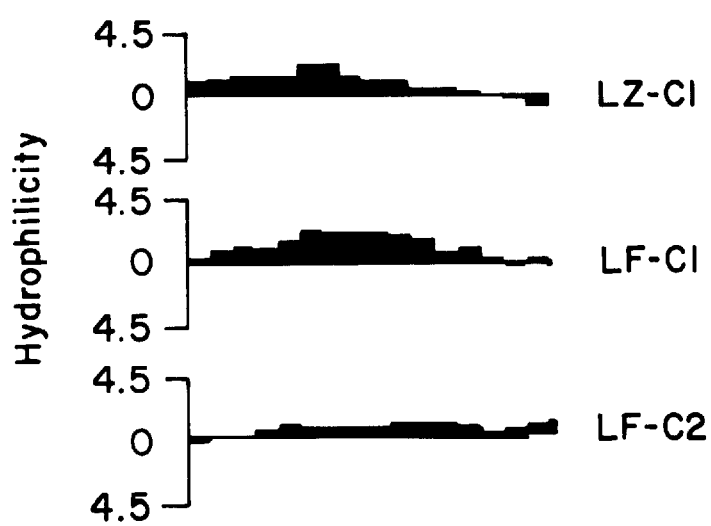
FIG. 5 presents evidence of a common AGE-binding cysteine-bounded loop (ABCD motif) within AGE-binding domains. A. Protein sequences of a common $CX_{15-16}C$ cysteine loop within the AGE-binding domains of lysozyme and lactoferrin are aligned. B. Hydrophilicity analysis of these peptides using the Hopp-Woods method (analyzed with MacVector 4.0 software, IBI, New Haven, Conn.). C. $^{25}$I-AGE-BSA ligand dot blot. Peptides corresponding to the cysteine loops of lysozyme (LZ-C1, SEQ ID NO:7) and lactoferrin (LF-C1, SEQ ID NO:8 (LF-C2, SEQ ID NO: 9)) were commercially synthesized (Bio-Synthesis, Inc. Lewisville, Tex.). LZ, LZ-C1, LF-C1, an unrelated 28 amino acid peptide, and insulin were immobilized on nitrocellulose membrane at 30 $\mu$g/dot under reducing conditions. The membrane was blocked with 1% BSA in PBS buffer and blotted with 1,000,000 cpm $^{25}$I-AGE-BSA for 1 hour in the presence (right column) or absence (left column) of 50-fold excess AGE-BSA. An autoradiograph is shown.

Although these AGE-binding domains in lysozyme and lactoferrin do not share homology in primary sequences, we identified a common 17–18 amino acid hydrophilic cysteine loop ($CX_{15-16}C$) in these AGE-binding peptides (FIG. 5A). Hydrophilicity analysis indicated that these loops are all hydrophilic (FIG. 5B). We named this putative AGE-binding cysteine-bounded loop domain an "ABCD" motif. Synthetic peptides corresponding to this ABCD loop of lysozyme (CNDGRIPGSRNLCNIPC, a.a. #62–78, SEQ ID NO: 7) and lactoferrin (CFQWQRNMRKVRGPPVSC, a.a. #8–25, SEQ ID NO: 8; and CLQ, a.a. #613–630 SEQ ID NO: 9) were constructed. These synthetic ABCD loop peptides, but not irrelevant control peptides, are capable of binding to $^{125}$I-AGE-BSA in ligand blot analysis (FIG. 5C). Interestingly, it was reported recently that the N-terminal cysteine loops of human and bovine lactoferrin (39% homology) are the bactericidal domain (Bellamy et al., 1992 Biochem. Biophys. Acta. 1121: 130), which may explain why AGE-binding to this loop blocked the bactericidal activity of lactoferrin. We further identify that this motif is also present in other members of antimicrobial proteins, such as defensins, azurocidin, neutrophil antibiotics, and seroprocidins (Gabay et al., 1993, Opin. Immunol. 5: 97; Leher et al., 1993, Annu. Rev. Immunol. 11: 105). It is also known that most bactericidal proteins are hydrophilic, at least over certain domains. Without any limitation by way of mechanism, the fact that this AGE-binding cysteine loop is apparently conserved across species and among defense proteins, may be responsible for the bacterial binding properties of these defense proteins. Glucose-modified proteins, like AGEs, may mimic molecular structures of the bacterial wall and bind to antibacterial proteins such as lysozyme and lactoferrin. High AGE levels in tissues and body fluids could form interactions with antibacterial proteins thus interfering with normal defense functions.

EXAMPLE 2: INHIBITION OF BACTERIAL GROWTH BY LYSOZYME WITH OR WITHOUT AGES

The following example provides evidence that the lysozyme-mediated inhibition of bacterial growth is compromised by AGE-complexes and, additionally, that the deleterious effect of AGEs on lysozyme activity may be overcome by the addition of lysozyme or a peptide derived therefrom. By administration of the peptide of the invention, or a similar derivative of lysozyme, the inhibition of lysozyme activity by AGE-complexes can be minimized through a titration of AGEs by the additional lysozyme or derivative thereof. Furthermore, titration of AGEs provides a general method of treating individuals suspected of increased levels of AGEs and would not only overcome inhibition of lysozyme activity by AGEs but also rescue other cellular components whose activities are diminished by AGE complexes in vivo.

Materials and Methods

Live *Micrococcus luteus* (ATCC 9341) at $2.5 \times 10^{-5}$ CFU/ml in Nutrient Broth (DIFCO) was incubated with lysozyme at concentrations of 0, 2, 10, 50, 250, 1250 and 3000 µg/ml plus 1.5 mg/ml AGE-BSA, AGE-ovalbumin, or BSA. Bacterial growth for different cultures was determined and based on visible bacterial growth after 18 hours incubation at 30° C.

Results

Addition of lysozyme to the bacterial cultures was a requirement to prevent bacterial growth, whether media was supplemented with BSA, AGE-BSA or AGE-ovalbumin and is shown in Table 1 below.

TABLE 1

Dose-dependent Inhibition of Bacterial Growth by Lysozyme with or without AGEs

| Lysozyme (µg/ml) | BSA | AGE-BSA | AGE-Ovalbumin |
| --- | --- | --- | --- |
| 3000 | − | − | − |
| 1250 | − | − | − |
| 250 | − | − | − |
| 50 | − | − | + |
| 10 | − | + | + |
| 2 | − | + | + |
| 0 | + | + | + |

Addition of AGE-BSA and AGE-ovalbumin to cultures required that larger amounts of lysozyme be added to overcome the AGE-mediated inhibition of lysozyme's bactericidal effects. Unmodified BSA did not show an antagonistic effect on the bactericidal activity of lysozyme. Concentrations of lysozyme greater than about 10 μg/ml were effective in re-establishing the activity of lysozyme in killing bacteria in cultures supplemented with AGE-BSA, while concentrations of over 50 μg/ml of lysozyme were necessary to obtain the same effect in AGE-ovalbumin supplemented cultures.

Discussion

This Example demonstrates that AGE-modified compounds are capable of inhibiting the normal bactericidal activity of lysozyme, shown by the inability of lysozyme to exhibit this activity at concentrations otherwise capable of producing the effect in the absence of AGE-modified compounds. Furthermore, this inhibition may be overcome by further addition of lysozyme, or an AGE-binding peptide derivative thereof, in a dose-dependent fashion. Thus, the administration of lysozyme, or an AGE-binding peptide domain thereof, to individuals suspected of increased levels of AGE-modified compounds can provide for a reduction of AGE levels and/or a reversal of the deleterious effects on lysozyme or other cellular components affected by AGEs.

EXAMPLE 3: DETECTION OF AGE-MODIFIED COMPOUNDS THROUGH AN ELISA-TYPE BINDING ASSAY UTILIZING LYSOZYME

Detection of AGE complexes in a sample has great significance in determining pathological levels of AGEs in blood or tissue of a subject or in any biological sample. This Example demonstrates such a detection method by adhering lysozyme, or a peptide comprising the AGE-binding domain thereof, although any homologous peptide providing a similar region of AGE binding capability can be employed, to a surface and incubating or passing a sample over the peptide to allow it to capture the AGE-modified molecules of the sample. A detector antibody raised against AGEs then can be used to detect the presence of AGE-modified components specifically bound to the adhering lysozyme or the AGE-binding peptide domain thereof.

Materials and Methods

In this Example, chicken lysozyme was first prepared in phosphate buffered saline (PBS) at a concentration of 30 mg/ml and reduced by addition of 2-mercaptoethanol at a final concentration of 2% (vol:vol). To adhere lysozyme to the ELISA plate, the reduced preparation of lysozyme was diluted in coating buffer (CB; 0.1M NaHCO$_3$, pH 9.6, with 0.02% NaN$_3$ w/v) to a final concentration of 100 μg/ml. Aliquots of 100 μl of this preparation were then applied to each well of a 96-well ELISA plate at 4° C. and incubated overnight to allow lysozyme to adhere to the plate. The plate was next washed three times in Wash Buffer (WB; PBS with 0.05% Tween-20, 1 mM NaN$_3$) and blocked with 150 μl/well SuperBlock (Pierce, cat. #37515) at room temperature for 1 h. Again, the plate was washed three times with WB, and AGE-BSA diluted with dilution buffer (DB; 0.2% Tween in PBS at pH 7.4) was added alone or with either 2% normal goat serum (NGS), 2% BSA, or 0.2% BSA and incubated at room temperature for 2 h on a shaker. A dilution series of a standard preparation of AGE-BSA was added to wells in triplicate, in concentrations that varied from 0.01 μg/ml—1000 μg/ml in increments of 10×. The specific activity of this AGE-BSA was approximately 1 Unit per 2.21 μg of AGE-BSA, assessed by a standard ELISA assay using a monoclonal anti-AGE antibody. After washing the plate with WB, an anti-AGE monoclonal antibody diluted with 2% NGS in DB was added and allowed to incubate at room temperature for 2 h with gentle shaking. The plate was washed 3× with WB and an alkaline phosphatase-conjugated anti-mouse antibody raised in goat or rabbit, for instance, (e.g. Cappel, cat. #59296), diluted 1:3000 in DB plus 1% NGS was added to the wells and incubated at 37° C. for 1 h. The plate was next washed and 1 mg/ml of p-nitrophenyl phosphate in substrate buffer (SB; 9.7 ml diethanolamine, 0.1 g MgCl$_2$.6H$_2$O, 0.2 g NaN$_3$ in 800 ml ddH$_2$O, pH 9.8, diluted to 1 L with ddH$_2$O) was added. The OD was measured at 405 nm after addition of substrate and once the highest OD was reached (approximately 60 min.).

Results

Figure 6:
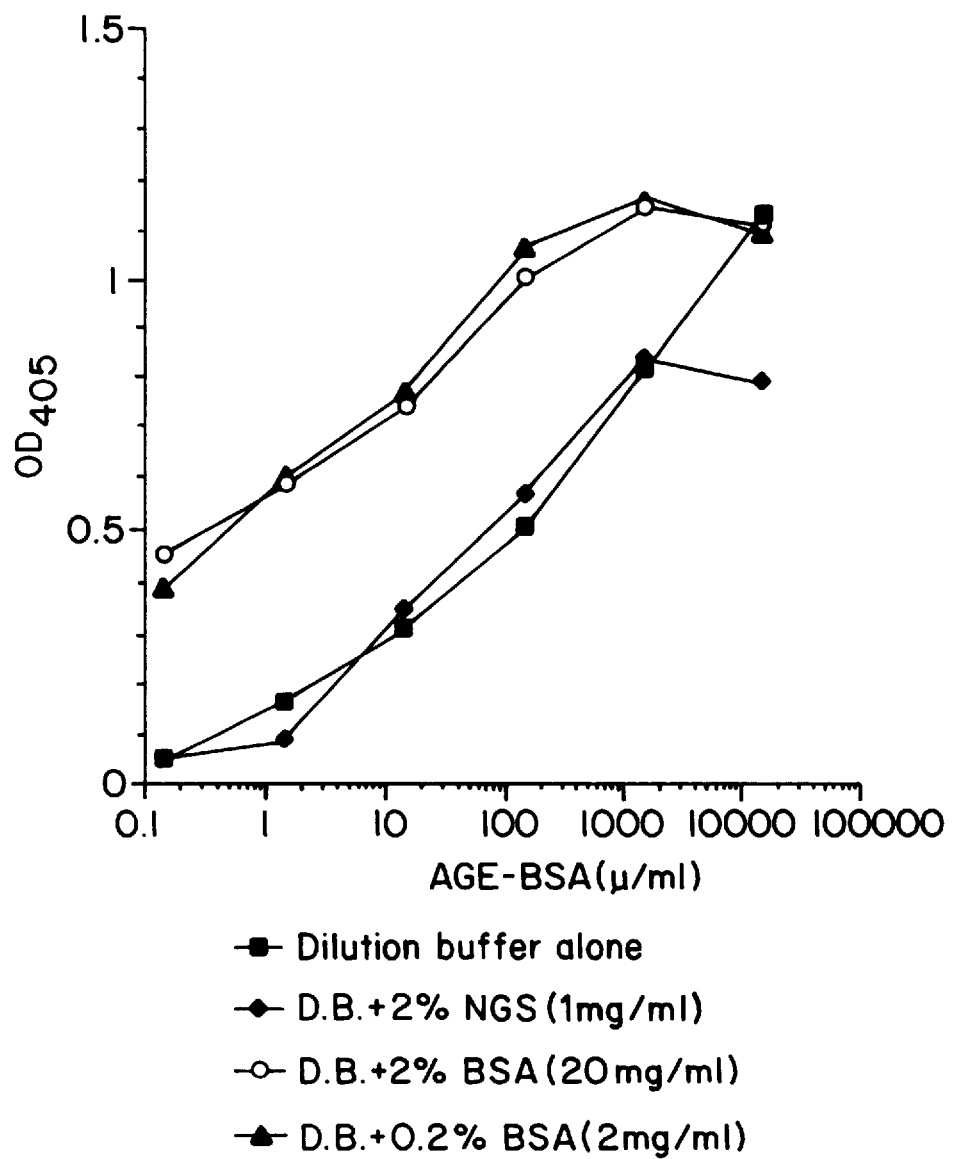
FIG. 6 demonstrates detection of AGE-BSA using a sandwich-type ELISA-based assay. Lysozyme immobilized on the assay plate captured AGE-BSA from the sample and the level of detection was related to the concentration of AGE-BSA in the sample. Chicken lysozyme was reduced by addition of 2-mercaptoethanol. Lysozyme was adhered to a plate and AGE-BSA was added alone or with either 2% normal goat serum (NGS), 2% BSA, or 0.2% BSA and incubated. Anti-AGE monoclonal antibody diluted in buffer with 2% NGS was added and allowed to incubate. Alkaline phosphatase-conjugated anti-mouse antibody and p-nitrophenyl phosphate were used to detect the presence of AGEs bound to lysozyme.

Detection of AGE-BSA by this sandwich-type ELISA-based assay was related to the concentration of AGE-BSA in the sample, regardless of whether excess purified protein was included in the sample dilution buffer or not (see FIG. 6). Interestingly, the apparent efficiency with which lysozyme captured and presented AGE-BSA in the sample to the detector antibody differed depending on the addition of BSA or NGS to the dilution buffer. When unmodified BSA was included in the sample dilution buffer in concentrations of 2% or 0.2%, the ability of lysozyme to detect AGE-BSA improved compared to parallel assays employing 2% NGS in DB or assays where sample dilution buffer was used alone. In all cases lysozyme captured AGE-BSA from the sample, in proportion to the AGE-BSA concentration, allowing the detector antibody to bind to the complex, thus measuring levels of AGE-compounds in the sample.

Discussion

From the graph depicting the assay results (see FIG. 6) of the present Example, the detection of AGE-BSA in an ELISA format based on AGE-binding by lysozyme is clearly demonstrated. The addition of BSA to the sample dilution buffer improved the level of detection of AGE-BSA in the sample, but AGE-modified BSA was detected if NGS was substituted or if no extra protein was included, demonstrating that the assay is capable of such detection. In this method the AGE-binding peptide domain of lysozyme, or an AGE-binding peptide homologous thereto, could be substituted for reduced lysozyme as the capture agent, and such variations are intended to be included within the scope of the invention. Various biological samples contemplated by the present Example, such as, but not limited to, blood, plasma, urine, and various types of tissue fluids or tissue extracts can be readily substituted for the AGE-BSA of the present Example, providing a method to determine the level of AGEs in such samples.

The detection of AGEs in a biological sample by the assay described in this Example is useful for monitoring the course of anti-AGE therapy and assessing the degree of AGE-modification to proteins for human use or consumption, as well as in other diagnostic applications. Likewise, other known ELISA-like assay formats, where lysozyme, or an AGE-binding peptide domain thereof, substitutes for an AGE-specific antibody, are included within the scope of this Example.

EXAMPLE 4: LOCALIZATION OF AGE-COMPOUNDS TO LYSOZYME-DERIVATIZED SUBSTRATUM AND SPECIFIC ELUTION OF AGE-COMPOUNDS THEREFROM

By immobilizing lysozyme or the AGE-binding peptide portion thereof, i.e. the peptide of the invention, to an affinity chromatographic column (e.g. by derivatizing the beads of the column with lysozyme), it is demonstrated that AGEs can bind to lysozyme, or any molecule with similar AGE binding domain, and be subsequently eluted therefrom with the addition of an appropriate eluant. This method not only provides a useful way to selectively bind AGE-modified molecules, but also provides a means to remove and sequester such AGE-modified molecules from complex mixtures, including biological fluids such as, for example, blood. If desired, the sequestered AGEs can be eluted from the column for use or analysis.

Methods

Cyanogen bromide-activated Sepharose 4B beads were derivatized with lysozyme, according to the manufacturer's instructions, and a 1.5 ml bed volume column was prepared (L-column). Likewise, a control column was established using beads derivatized with BSA (BSA-column). The columns were then loaded with 500 $\mu$l of 6 mg/ml AGE-BSA and subsequently washed extensively with PBS. Elution of AGE-BSA from the column was achieved by addition of 0.1N NaOH and 200 $\mu$l fractions were collected. Eluted fractions were neutralized with 1N HCl.

Results

Figure 7:
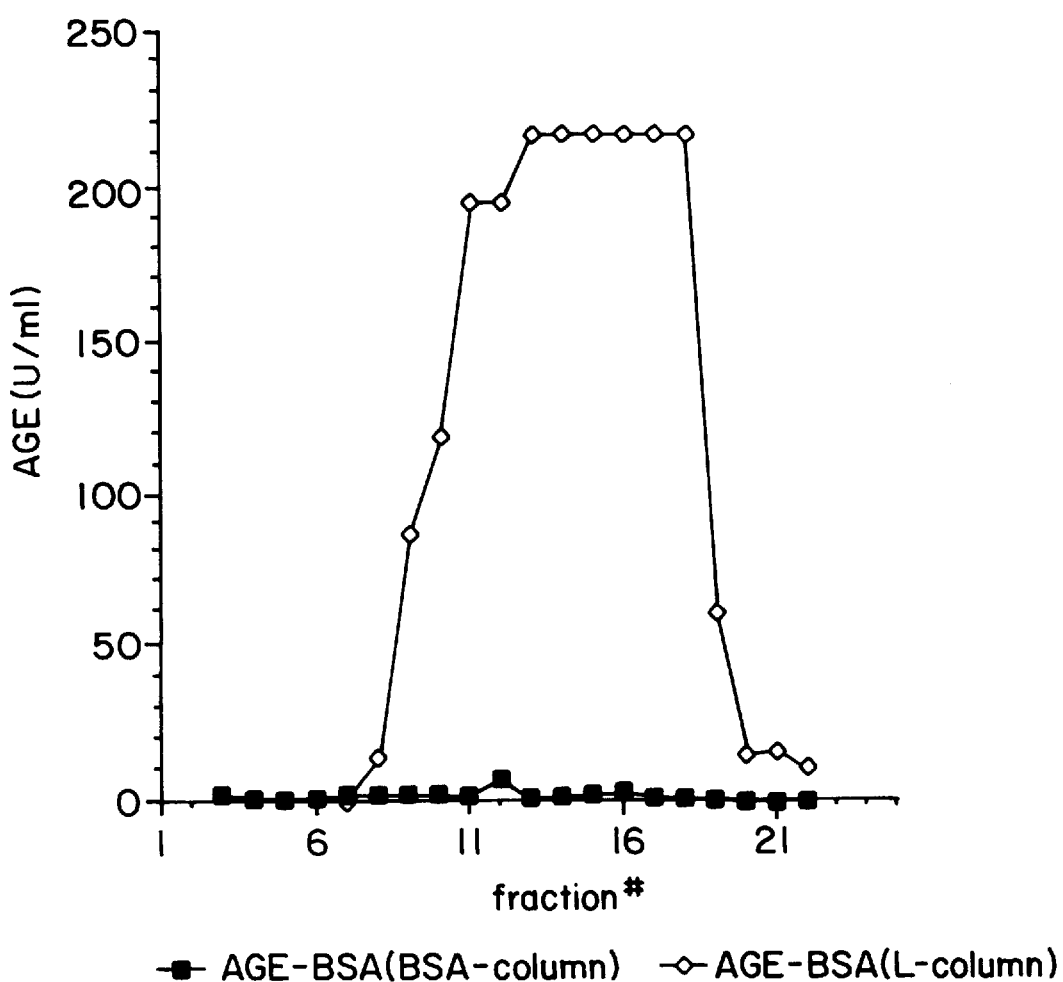
FIG. 7 shows in U/ml (1 Unit is defined as the competetive activity of a 1:5 dilution of normal human serum against α-AGE antibody binding to an AGE-BSA coated plate) the amounts of AGE-BSA which bound and were eluted from a chromatographic column of lysozyme- or BSA-derivatized beads. Cyanogen bromide-activated Sepharose 4B beads were derivatized with lysozyme and a control column was established using BSA-derivatized beads. The columns were loaded with AGE-BSA and washed thoroughly; AGE-BSA remained bound to the column. Specific elution of AGE-BSA from the lysozyme-column was achieved by addition of 0.1N NaOH.

FIG. 7 shows, in U/ml (1 Unit is defined as the competetive activity of a 1:5 dilution of normal human serum against $\alpha$-AGE antibody binding to an AGE-BSA coated plate), the amounts of AGE-BSA which bound and were eluted from the lysozyme- or BSA-column. AGE-BSA was found to bind to the lysozyme column, which became visibly colored as yellow-brown AGE pigments associated with the lysozyme-derivatized beads, and the AGE pigments and AGE immunoreactivity eluted as a peak centered at fractions 12–18. It was clear that little or no AGE-BSA bound to the BSA-column (no browned pigments bound to the column to make it visibly colored); there was correspondingly virtually no recovery of AGE immunoreactivity during the elution step.

Discussion

The specificity of AGE binding to lysozyme is evident in the experiments of the present Example. The data demonstrate that AGE-BSA binds to lysozyme which has been chemically attached to chromatography beads. This bound AGE-protein was shown to reversibly dissociate when a suitable eluant was applied. Although NaOH was the eluant used in the present Example any solution capable of causing AGE-modified compounds to be removed from the inunobilized lysozyme could be employed, including high tonicity solutions, chaotropic agents, or another AGE preparation. In contrast to data obtained using the lysozyme-column, little or no AGE-BSA was eluted from the BSA-column, further demonstrating that AGE-binding is a specific property of lysozyme and its AGE-binding domain.

The use of such a column as described in this Example provides one skilled in the art with the ability to specifically screen a sample possibly containing AGE-modified compounds by contacting the sample to the column under conditions which can permit binding of AGEs to the column. The applications of such procedure can include, but are certainly not limited to, determination of an amount of AGEs in a sample, partitioning AGEs from a sample as in, for example, hemodialysis, or recovering AGEs from a sample.

Additionally, lysozyme, or a peptide portion thereof capable of binding to AGEs, can be cross-linked to entities other than beads for chromatographic and other uses, for instance, to thereby generate specific targeting agents to localize the conjugate molecule to AGEs. For example, rather than Sepharose beads, a dye or pigment can be attached or conjugated to lysozyme, or the peptide of the invention, and then contacted to AGEs and allowed to bind under appropriate conditions. The result is the localization of the conjugated molecule to an AGE-modified surface. Any tissue which is manifested with AGEs, such as skin or tooth enamel, can be, contacted with such AGE-binding peptide/dye conjugate, for example, to localize the conjugate function to the AGEs. Additionally, a molecule linked to lysozyme or an AGE-binding peptide domain thereof, can be used as a marker for identification of specific tissues containing elevated levels of AGE modifications or AGE-modified compounds.

Colorants that may be useful in the present invention include pigments such as titanium dioxide, as well as other dyes that, for example, may be suitable for food, drug and cosmetic applications, and known as FD&C dyes and the like. Illustrative examples include indigoid dye, known as FD&C Blue No. 2, which is the disodium salt of 5,5'-indigotindisulfonic acid. Similarly, the dye known as FD&C Green No. 1 comprises a triphenylmethane dye and is the monosodium salts of 4-[4-N-ethyl-p-sulfobenzylamino) diphenylmethylene]-[1-(N-ethyl-N-p-sulfoniumbenzyl)-2-5-cyclohexadieneimine]. A full recitation of all FD&C and D&C and their corresponding chemical structures may be found in the *Kirk-Othmer Encyclopedia of Chemical Technology*, in Volume 5, pages 857–884, which text is accordingly incorporated herein by reference.

In a further embodiment of the invention, the compounds or constructs described above may be prepared for use in the delivery of active agents or ingredients, such as disinfectants, anti-fungal and anti-microbial agents, and other therapeutics, to the site of an infection, infestation or the like, whether in direct contact with a mammal or not. Accordingly, a compound of this type may comprise the molecule having the hydrophilic loop domain of the invention, together with a particle or bead and the active ingredient of interest. In a specific instance, the compound may be prepared to facilitate the extended or delayed release of the active ingredient, as by the formulation of the bead or the coating thereof with a composition that is limited in solubility or is foraminous, in the latter instance to permit the ratable release of the active as by leaching. Suitable compositions include pH-sensitive enteric coating materials such as cellulose acetate phthalate, polyvinyl acetate phthalate, hydroxypropylmethylcellulose phthalate, hydroxypropylmethylcellulose acetate succinate, methacrylic acid copolymers, as well as other coating materials such as hydroxyethyl cellulose, hydroxypropyl cellulose, shellac, and mixtures. Naturally, the foregoing list is representative and non-limitative of materials that may be used in the preparation of suitable extended-release formulations.

EXAMPLE 5: OPSONIZATION OF AGE-PROTEINS BY LYSOZYME LEADS TO ENHANCED UPTAKE BY MACROPHAGES

The following provides by way of example a means of removing AGE-compounds from the blood or other tissue of a subject by increasing the uptake of such AGEs by phagocytosis. By combining AGEs with a suitable opsonin, i.e. the lysozyme molecule of the invention or an AGE-binding peptide domain of or related to the AGE-binding domain of the present invention which is found in lysozyme, it is possible to achieve the opsonization of AGE-modified compounds and thereby enhance the removal of such compounds from a tissue, from the circulation, or from the body.

Materials and Methods

To determine the rate and extent of uptake of AGE-modified molecules by macrophages in vitro, $10^6$ mouse macrophage cells (e.g. RAW 264.7 cells) were cultured in a 24-well tissue culture plate containing I ml RPMI medium. Two to three $\mu$g of $^{125}$I labeled lysozyme, -BSA, or -AGE-BSA were next added in conjunction with 50-fold excess of either unlabeled lysozyme, AGE-BSA, or both lysozyme and AGE-BSA. Cells were incubated at 37° C. for 2 h and then washed 5 times in RPMI medium. Cells were next removed from the plate by gentle scraping into microfuge tubes, centrifuged at 400×g for 5 min. and washed two more times. The washed pellet was examined with a gamma-counter for detection of levels of $^{125}I$ taken up by the cells.

Results

Figure 8:
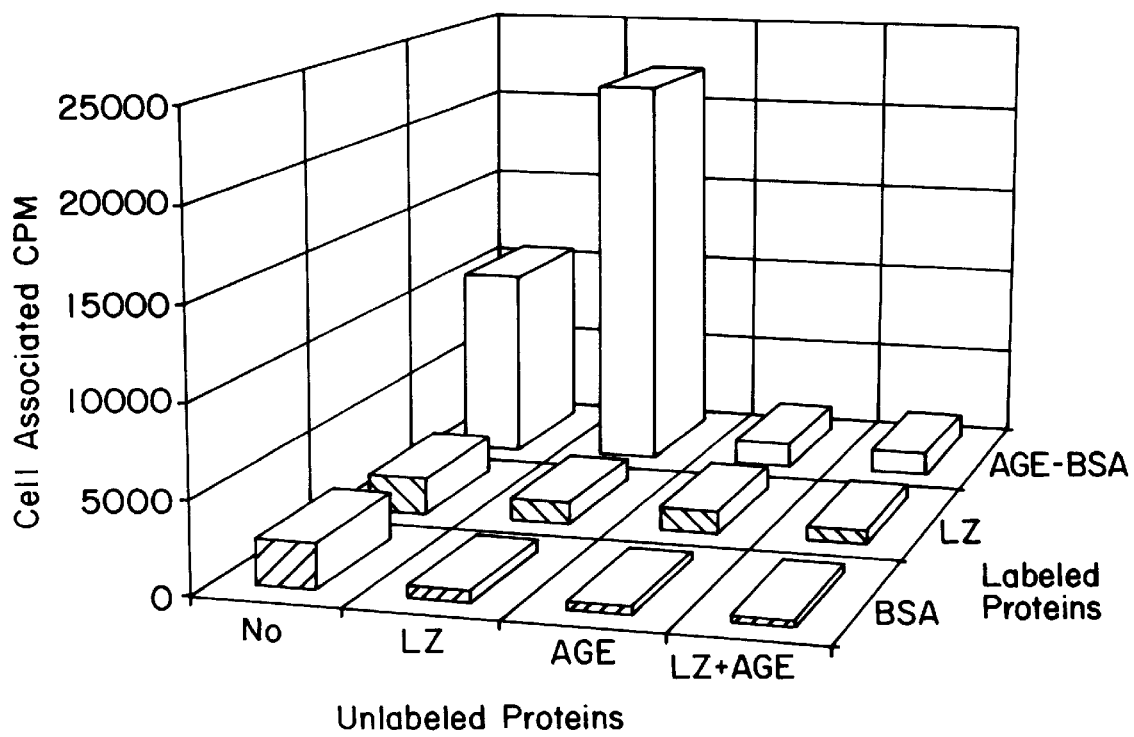
FIG. 8 shows uptake of AGE-modified molecules by macrophages and that addition of lysozyme to medium containing labeled AGE-BSA causes an increase in uptake of AGE-BSA by macrophage cultures. Mouse macrophage cells were cultured with $^{125}$I-labeled lysozyme, -BSA, or -AGE-BSA and in conjunction with 50-fold excess of either unlabeled lysozyme, AGE-BSA, or both unlabeled lysozyme and AGE-BSA. Cells were incubated at 37° C. for 2 h and then washed. A gamma-counter measured the amounts of $^{125}$I taken up by the cells.

By reference to FIG. 8, it can be seen that addition of labeled AGE-BSA to the media allows the AGE-mediated uptake of this substrate by macrophages to be quantified and that AGE-BSA is taken up at an enhanced rate compared to labeled but otherwise unmodified-BSA or lysozyme. Additionally, supplementing either labeled BSA or labeled lysozyme with lysozyme did not result in further uptake of these labeled molecules by macrophage cultures, whereas the addition of lysozyme to solutions of labeled AGE-BSA caused a 2-fold increase in uptake of AGE-BSA by macrophage cultures. This indicates that lysozyme aids in the uptake of AGE-modified molecules by macrophages and can thereby reduce the levels of the AGE compound in the surrounding media.

Discussion

The present Example represents an important but previously unanticipated aspect of lysozyme activity which, when applied in vivo, can have significant therapeutic value to an individual suffering from deleterious levels of AGEs. The difference between the amount of uptake of labeled AGE-BSA by macrophages when lysozyme is added or omitted from a sample indicates that lysozyme, or a molecule with similar AGE-binding and opsonization activity, can be used to potentiate the phagocytosis of these compounds and thus their removal from blood, tissue, or the body. The net impact would be a decrease in levels of AGE-modified compounds in the tissue or blood, for example, of the individual afflicted with unhealthy amounts of AGEs.

In summary, we demonstrate that a hydrophilic cysteine loop-bounded (ABCD motif) in two major naturally existing antimicrobial proteins, lysozyme and lactoferrin, is responsible for AGE-protein binding; binding to AGE blocks lysozyme- and lactoferrin-mediated enzymatic and bactericidal activity. We postulate that elevated levels of AGEs in diabetic patients may inhibit the bactericidal activity of endogenous antimicrobial proteins, such as lysozyme and lactoferrin. Furthermore, by administering lysozyme, or a peptide with similar AGE-binding capabilities, to individuals suspected of having unhealthy levels of AGEs, it is possible to decrease these harmful levels of AGEs and thereby re-establish the bactericidal activity of the host antimicrobial proteins.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

---

What is claimed is:

1. A method for inhibiting cross-linking of advanced glycosylation endproducts (AGEs) in a subject suspected of having elevated levels of AGEs, comprising administering to the subject an amount of an AGE-binding molecule effective to bind AGEs and inhibit cross-linking thereof, said molecule having at least one structure corresponding to $R_1Cys_1Xaa_nCys_2R_2$ (SEQ ID NOS: 1–9), wherein $Cys_1$ and $Cys_2$ may be cross-linked and $Cys_1$ and $Cys_2$ together with $Xaa_n$ is an AGE-binding, hydrophilic peptide sequence; $R_1$ and $R_2$ are each independently a polypeptide, a $C_1$ to $C_{12}$ alkyl, aryl, heteroalkyl, or heteroaryl group, or hydrogen; Xaa is any α-amino acid; and n=13–18; and wherein the hydrophilic nature of the peptide sequence is determined by the Hopp-Woods method.

2. The method according to claim 1, wherein n=15–16.

3. The method according to claim 1, wherein the hydrophilic peptide seqience is selected from the group consisting of SEQ ID NOS:7–9.

4. The method according to claim 1 wherein the molecule is lysozyme.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: Internal ( x i ) SEQUENCE DESCRIPTION: SEQ ID NO:1:

Cys Xaa Xaa Xaa Xaa Xaa Xaa Xaa Xaa Xaa Xaa Xaa Xaa Xaa Cys
 1                     5                        10                     15

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v ) FRAGMENT TYPE: Internal ( x i ) SEQUENCE DESCRIPTION: SEQ ID NO:2:

Cys Xaa Xaa Xaa Xaa Xaa Xaa Xaa Xaa Xaa Xaa Xaa Xaa Xaa Xaa Cys
 1                     5                        10                     15

( 2 ) INFORMATION FOR SEQ ID NO:3:

( i ) SEQUENCE CHARACTERISTICS:
            ( A ) LENGTH: 17 amino acids
            ( B ) TYPE: amino acid
            ( D ) TOPOLOGY: linear ( i i ) MOLECULE TYPE: peptide ( v ) FRAGMENT TYPE: Internal ( x i ) SEQUENCE DESCRIPTION: SEQ ID NO:3:

Cys  Xaa  Xaa  Xaa  Xaa  Xaa  Xaa  Xaa  Xaa  Xaa  Xaa  Xaa  Xaa  Xaa  Xaa  Xaa  Cys
 1                    5                             10                            15

( 2 ) INFORMATION FOR SEQ ID NO:4:

( i ) SEQUENCE CHARACTERISTICS:
            ( A ) LENGTH: 18 amino acids
            ( B ) TYPE: amino acid
            ( D ) TOPOLOGY: linear ( i i ) MOLECULE TYPE: peptide ( v ) FRAGMENT TYPE: Internal ( x i ) SEQUENCE DESCRIPTION: SEQ ID NO:4:

Cys  Xaa  Xaa  Xaa  Xaa  Xaa  Xaa  Xaa  Xaa  Xaa  Xaa  Xaa  Xaa  Xaa  Xaa  Xaa
 1                    5                             10                            15

Xaa  Cys ( 2 ) INFORMATION FOR SEQ ID NO:5:

( i ) SEQUENCE CHARACTERISTICS:
            ( A ) LENGTH: 19 amino acids
            ( B ) TYPE: amino acid
            ( D ) TOPOLOGY: linear ( i i ) MOLECULE TYPE: peptide ( v ) FRAGMENT TYPE: Internal ( x i ) SEQUENCE DESCRIPTION: SEQ ID NO:5:

Cys  Xaa  Xaa  Xaa  Xaa  Xaa  Xaa  Xaa  Xaa  Xaa  Xaa  Xaa  Xaa  Xaa  Xaa  Xaa
 1                    5                             10                            15

Xaa  Xaa  Cys ( 2 ) INFORMATION FOR SEQ ID NO:6:

( i ) SEQUENCE CHARACTERISTICS:
            ( A ) LENGTH: 20 amino acids
            ( B ) TYPE: amino acid
            ( D ) TOPOLOGY: linear ( i i ) MOLECULE TYPE: peptide ( v ) FRAGMENT TYPE: Internal ( x i ) SEQUENCE DESCRIPTION: SEQ ID NO:6:

Cys  Xaa  Xaa  Xaa  Xaa  Xaa  Xaa  Xaa  Xaa  Xaa  Xaa  Xaa  Xaa  Xaa  Xaa  Xaa
 1                    5                             10                            15

Xaa  Xaa  Xaa  Cys
                    20

( 2 ) INFORMATION FOR SEQ ID NO:7:

( i ) SEQUENCE CHARACTERISTICS:
            ( A ) LENGTH: 17 amino acids
            ( B ) TYPE: amino acid
            ( C ) STRANDEDNESS: single
            ( D ) TOPOLOGY: linear (i i) MOLECULE TYPE: peptide
    (A) DESCRIPTION: LZ-C1, 62-78

(i i i) HYPOTHETICAL: NO (i v) ANTI-SENSE: NO (v) FRAGMENT TYPE: internal (x i) SEQUENCE DESCRIPTION: SEQ ID NO:7:

Cys Asn Asp Gly Arg Ile Pro Gly Ser Arg Asn Leu Cys Asn Ile Pro
 1               5                   10                  15

Cys (2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: single
        (D) TOPOLOGY: linear (i i) MOLECULE TYPE: peptide
        (A) DESCRIPTION: LF-C1, 8-25

(i i i) HYPOTHETICAL: NO (i v) ANTI-SENSE: NO (v) FRAGMENT TYPE: internal (x i) SEQUENCE DESCRIPTION: SEQ ID NO:8:

Cys Phe Gln Trp Gln Arg Asn Met Arg Lys Val Arg Gly Pro Pro Val
 1               5                   10                  15

Ser Cys (2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: single
        (D) TOPOLOGY: linear (i i) MOLECULE TYPE: peptide
        (A) DESCRIPTION: LF-C2, 613- 630

(i i i) HYPOTHETICAL: NO (i v) ANTI-SENSE: NO (v) FRAGMENT TYPE: internal (x i) SEQUENCE DESCRIPTION: SEQ ID NO:9:

Cys Leu Phe Gln Ser Glu Thr Lys Asn Leu Leu Phe Asn Asp Asn Thr
 1               5                   10                  15

Gly Cys